United States Patent [19]

Ueno

[11] Patent Number: 4,650,560

[45] Date of Patent: Mar. 17, 1987

[54] OXYGEN SENSOR

[75] Inventor: Sadayasu Ueno, Katsuta, Japan

[73] Assignee: Hitachi, Ltd., Tokyo, Japan

[21] Appl. No.: 816,840

[22] Filed: Jan. 7, 1986

[30] Foreign Application Priority Data

Jan. 25, 1985 [JP] Japan .................................. 60-10899

[51] Int. Cl.$^4$ ........................................... G01N 27/58
[52] U.S. Cl. .................................. 204/410; 204/412;
204/425; 204/426
[58] Field of Search ................. 204/425, 426, 412, 15,
204/410

[56] References Cited

U.S. PATENT DOCUMENTS 4,601,809  7/1986  Kitahara .............................. 204/406

FOREIGN PATENT DOCUMENTS 154451  12/1980  Japan .................................. 204/425
130261   9/1983  Japan .................................. 204/425

Primary Examiner—G. L. Kaplan
Attorney, Agent, or Firm—Antonelli, Terry & Wands

[57] ABSTRACT

An oxygen sensor, suited for measuring the concentration of an oxygen gas contained in an exhaust gas of an automobile, comprises a cell and a heater which is mounted for heating the cell. The heater, including an electrically insulating substrate and a heating element embeded in the substrate, has a recess on one surface thereof and a pair of side wall portions formed by forming the recess. The cell comprises a solid-electrolyte body, a detection electrode, a reference electrode and a chamber enclosing the reference electrode except for its opening. The cell is disposed in the recess of the heater and joined to the heater with an intermediate layer being disposed between the cell and the heater and sintered. The intermediate layer has a number of fine cracks and an intermediate thermal expansion coefficient between these of the solid-electrolyte and the substrate.

11 Claims, 16 Drawing Figures

1

OXYGEN SENSOR

BACKGROUND OF THE INVENTION

The present invention relates to an oxygen sensor, and particularly to an oxygen sensor suited for measuring the concentration of an oxygen gas contained in an exhaust gas of an automobile.

An oxygen sensor of this kind has a heater attached to a cell, and as for its manufacturing technique, the following methods are proposed, one of which is described in Japanese Utility Model Laid-Open No. 130,261/1983 in which green sheets of $ZrO_2$ and $Al_2O_3$ as cell elements and an electric insulating substrate, respectively are formed, electrodes, heaters, etc. are printed on the green sheets, and they are laminated and then sintered simultaneously without using a bonding agent. The other method is disclosed in Japanese Patent Laid-Open No. 154,451/1980 in which a cell formed of a thin or thick film of stabilized $ZrO_2$ is superposed in a layer on a heater of an $Al_2O_3$ base sintered beforehand and then is sintered to be joined to the latter by heat treatment also without using a bonding agent.

Since the $ZrO_2$ and $Al_2O_3$ layers have different thermal expansion coefficients, stresses are caused in the joint interface between the two layers by a difference in thermal expansion due to a heat cycle between the operating condition (600° to 900° C.) of an apparatus and the stationary condition (a room temperature) thereof, and this tends to cause exfoliation, cracking or the like. Moreover, simultaneous sintering of both materials, which is often the practice, causes problems such as insufficient strength of $Al_2O_3$ due to insufficient sintering thereof, and a reduction in electric resistance due to adding too much sintering aid.

SUMMARY OF THE INVENTION

An object of the present invention is to provide an oxygen sensor constructed of a cell and a heater which are formed of ceramic materials having different thermal expansion coefficients and which are joined to each other so that a joint portion is proof against a heat cycle and a thermal shock and allows the heater to heat the cell with excellent heat conduction.

The present invention is characterized in that: in view that a ceramic material sometimes shows a nonlinear displacement of considerable hysteresis due to phase transition in relation to thermal behavior, a cell and a heater formed of ceramic materials having different thermal expansion coefficients are joined to each other with an intermediate layer interposed between the cell and the heater and absorbing or buffering the amount of displacement of the joint interface between the cell and the heater.

According to a preferable aspect of the present invention, the heater structural member is so formed that the cell is surrounded by and embedded in the heater, thereby to increase the durability of the joining strength, and the intermediate layer is interposed between the cell and the heater so that the cell is brought into a close contact with the structural member of the heater during a period when they are under heating and that the cell is held in the heater to be prevented from dropping out during a period when they are not heated.

In order to stabilize the temperature of the cell so that the cell retain a required accuracy in detection in the condition that the seneor is exposed to a gas to be inspected which shows frequent fluctuation in temperature, the cell is surrounded by the structural member of the heater except for the portion of the detection electrode thereof, while a porous protective film may be provided on the detecting portion of the cell. It is preferable to use a means to impart negative feedback control on the heating power of the heater based on an electric signal representing the temperature of the cell.

DESCRIPTION OF THE PREFERRED EMBODIMENTS

An embodiment of an oxygen sensor according to the present invention will be described hereunder in detail, referring to FIGS. 1 to 12.

Figure 1A:
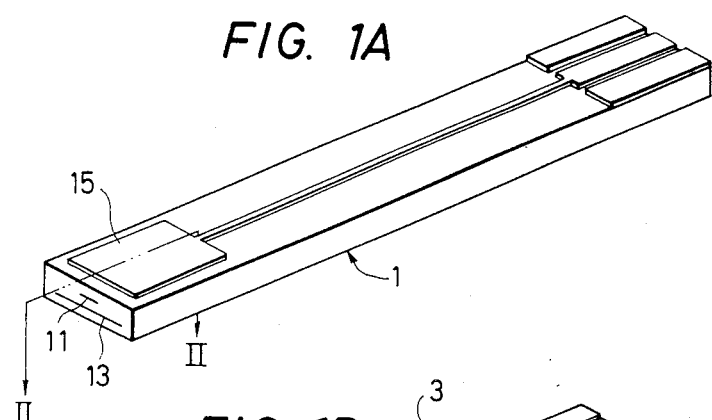
FIG. 1A is a perspective view of a cell used for an embodiment of the present invention.
Figure 1B:
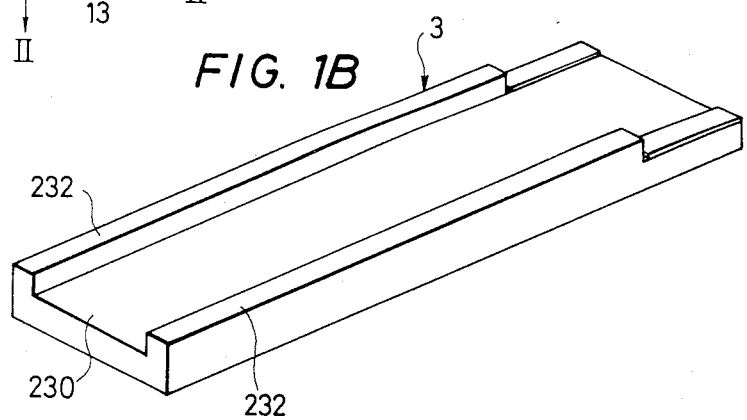
FIG. 1B is a perspective view of a heater according to an embodiment of the present invention.
Figure 2:
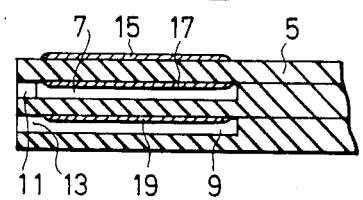
FIG. 2 is a sectional view of the cell taken along a line 2—2 of FIG. 1A.
Figure 3:
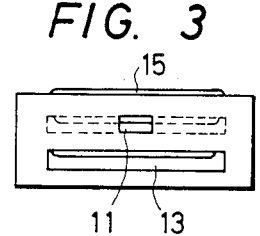
FIG. 3 is a side view of the cell of FIG. 2.

In FIGS. 1A and 1B showing a cell and a heater, respectively, the oxygen sensor comprises a cell 1, a heater 3 and an intermediate layer (not shown in FIGS. 1A,1B and will be described later) attaching the cell 1 to the heater 3. The cell 1 consist of two cell parts which are superposed on each other as shown in FIGS. 2 and 3. One outputs a signal proportional to the concentration of oxygen, while the other shows a switching output characteristic at an oxygen concentration point corresponding to the theoretical air-fuel ratio point. The cell 1 is described referring to FIGS. 2 and 3.

Figure 4:
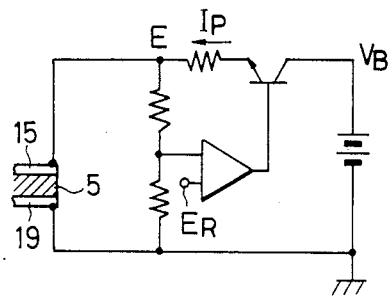
FIG. 4 is an electric circuit used for the cell shown in FIG. 2.

A solid-electrolyte body 5 of $Y_2O_3$-stabilized $ZrO_2$ consists of three layers which are joined to be one piece, and has two chambers 7, 9 which are formed in parallel with each other and extend along the length direction of the solid-electrolyte body 5. The chamber 7 has a narrow slit-like opening 11 at one end of the cell 1 while the chamber 9 has a relatively wide slit-like opening 13 at the same end as the above opening 11. A pair of porous electrodes 15 and 17 are formed opposite to each other so as to sandwich a part of the solid-electrolyte body 5. The electrode 15 is mounted on the upper surface of the solid-electrolyte body 5, and the electrode 17 is joined to the surface of a wall part defining the chamber 7. In the chamber 9, another porous electrode 19 is provided which is made in a pair with the electrode 15. The electrodes 15, 17 and 19 have a power of adsorbing and dissociating an oxygen gas ($O_2$) and formed of platinum, for instance. The electrode 15 is called a detection electrode which is exposed to a gas to be inspected and dissociates into the gas the oxygen ions coming from the opposite electrode 19. This electrode 19 is called a reference electrode, which has a number of fine openings and is exposed into a space formed around the electrode and partitioned from the surrounding gas to be inspected, that is, a diffusion chamber 9. This diffusion chamber 9 and the gas to be inspected communicate with each other through the opening 13 for diffusion. When a current $I_P$ is made to flow from the detection electrode 15 to the reference electrode 19 as shown in FIG. 4 while the temperature of the solid-electrolyte body 5 is 600° to 800° C., the oxygen in the diffusion chamber 9 is adsorbed to and ionized by the reference electrode 19, and the oxygen ions thus formed are pumped out through the solid-electrolyte body 5. As a result, the concentration of the oxygen on the reference electrode 19 side turns constantly smaller than that on the detection electrode 15, and thus an electromotive force of a concentration cell is induced. An induced electromotive force $=1$ V, for instance, can be obtained, according to Nernst's equation, when the temperature of the solid-electrolyte body 5 is 700° C. and when the oxygen concentration ratio between the detection electrode 15 and the reference electrode 19 is of 20 figures. Since the oxygen in the gas to be inspected is regulated in speed selectively in the diffusion opening 13 when it is diffused into the diffusion chamber 9, all of it is pumped out sequentially; consequently, the current thus induced shows a corresponding threshold value when the concentration $P_0$ of the oxygen in the gas to be inspected is constant.

Figure 5:
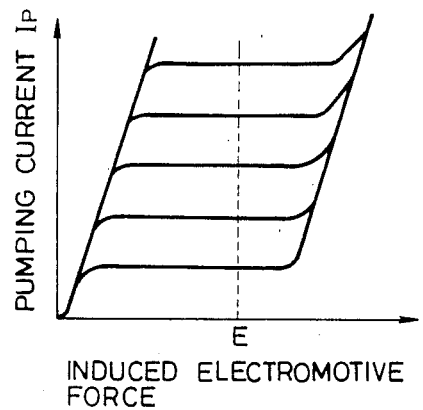
FIG. 5 is a graph showing a characteristic of the cell.

Therefore, the proportional relationship between the concentration $P_0$ of the oxygen in the gas to be inspected and $I_P$ is established by applying a feedback to the current $I_P$ by an electronic circuit so that the induced electromotive force E between the detection electrode 15 and the reference electrode 19 may take a prescribed value, for instance. FIG. 5 shows this relationship.

Figure 6:
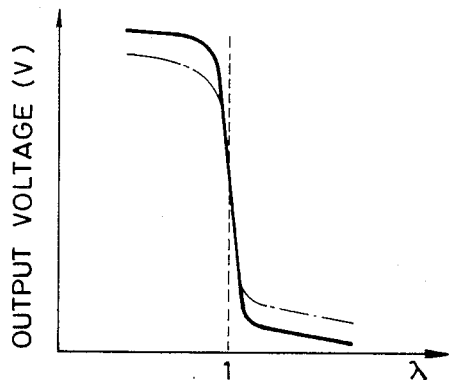
FIG. 6 is a graph showing a characteristic of the cell.

The cell part of the opposite electrodes 15-17 has a different usage from that of the above-mentioned cell part. The cell part is an oxygen concentration cell, in which oxygen is pumped constantly from the detection electrode 15 into the chamber 7 surrounding the reference electrode 17 for reserving the oxygen, an excess oxygen escapes out of the chamber 7 through the opening 11, and thus the concentration thereof is maintained virtually at a value approximating the concentration of oxygen in the atmosphere. Based on this value as a reference, the concentration of the oxygen around the detection electrode 15 is measured according to Nernst's equation on the concentration cell. The output characteristic in this case is that: when platinum is used for the detection electrode 15, the catalytic function thereof makes the concentration of oxygen around the detection electrode 15 smaller by about 20 figures than that around the reference electrode 17 in a region in which fuel is more concentrated than the one at a theoretical air-fuel ratio point. FIG. 6 shows the output characteristic of the cell of $O_2$ sensor for an automobile showing the theoretical air-fuel ratio point.

As above-described two cell parts are superposed to form an oxygen sensor. One outputs a signal proportional to the concentration of oxygen and has a large temperature dependence, while the other shows a switching output characteristic at an oxygen concentration point corresponding to the theoretical air-fuel ratio point and the temperature dependence at that point is small. The cell 1 including the two cell parts superposed in layers are joined to the heater 3. The cell 1 is joined to the heater 3 so that the cell part outputting a proportional signal is opposed to the heater 3, thereby both the cell parts can be improved in the temperature dependence.

Referring to FIGS. 7 to 12, the oxygen sensor in which the cell 1 is embedded in the heater 3 is described hereinunder in detail.

Figure 7:
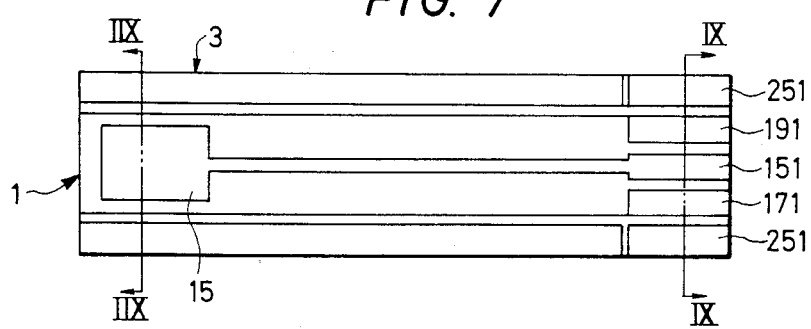
FIG. 7 is a plane view of an oxygen sensor in which the cell is attached to the heater.

FIG. 7 shows a plane view of the oxygen sensor in which the cell 1 is formed in a plate and elongated and is embedded in the heater 3. The cell is provided with the chambers 7, 9 and various electrodes 15, 17, 19 at one end portion, and various terminals at the other end.

Figure 8:
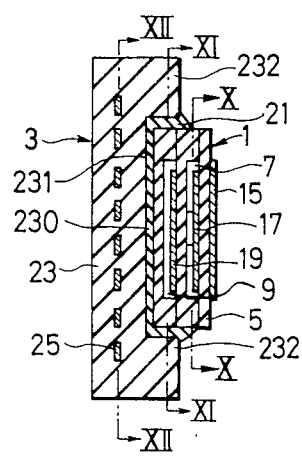
FIG. 8 is a sectional view of the cell taken along a line 8—8 of FIG. 7.
Figure 9:
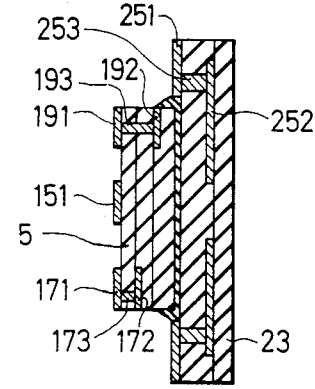
FIG. 9 is a sectional view of the cell taken along a line 9—9 of FIG. 7.

Referring to FIGS. 8 and 9, the cell 1 is provided, at one end, with the electrodes 15, 17 and 19 as mentioned above, and, at the other end, with terminals 151, 171 and 191 which are electrically connected to the electrodes 15, 17 and 19, respectively.

Figure 10:
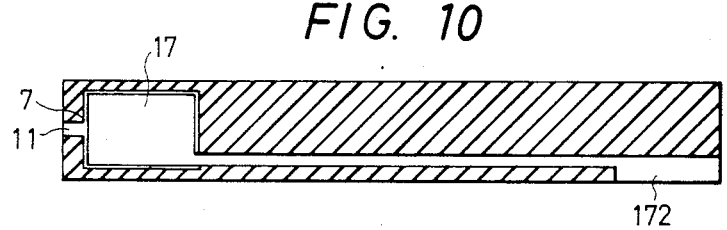
FIG. 10 is a sectional view of the cell taken along a line 10—10 of FIG. 8.
Figure 11:
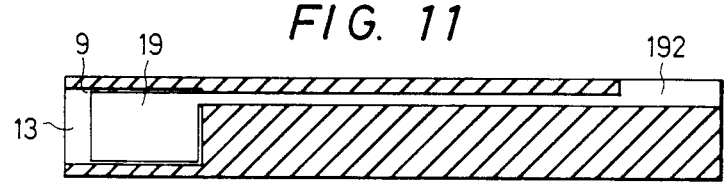
FIG. 11 is a sectional view of the cell taken along a line 11—11 of FIG. 8.
Figure 12:
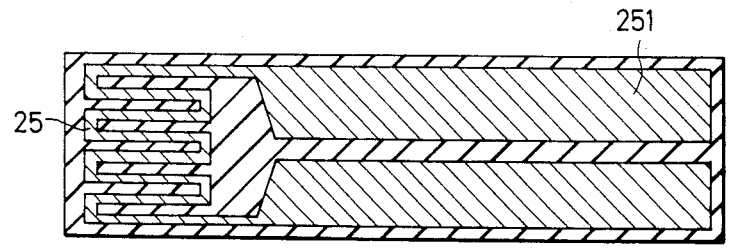
FIG. 12 is a sectional view of the cell taken along a line 12—12 of FIG. 8.

As shown in FIGS. 9 and 10, the reference electrode 17 is disposed in the reserving chamber 7 with the opening 11 and has a lead portion 172 which is electrically connected to the terminal 171 through a lead 173 inserted in a through hole formed in the solid-electrolyte body 5. The reference electrode 19 is disposed in the diffusion chamber 9 with the opening 13 and has a lead portion 192 which is electrically connected to the terminal 191 through a lead 193 inserted in a through hole made in the solid-electrolyte body 5 as shown in FIGS. 9 and 11.

Thus formed cell 1 is incorporated into the heater 3.

The heater 3 comprises an electrically insulating substrate 23 and a heating element 25 embedded in the substrate 23. The substrate 23 is made of $Al_2O_3$ as a principal component, that is, $Al_2O_3$-base ceramics and tungsten oxide and its plate-like shape arc preferable for the heating element 25. The heating element 25 is arranged in a zigzag shape around the chambers 7, 9. Both the ends 252 of the heating element 25 are electrically connected to the terminals 251 through leads 253 inserted in through holes made in the substrate 23.

The substrate 23, which is made in plate, has a recess 230 of a substantially rectangular cross section, which is elongated in its length direction, as best shown in FIG. 1B. The recess 230 makes a pair of side wall portions 232 at both the sides of the recess 230 so as to project from a bottom surface 231, thereby providing a U-shaped cross section. An adhesive is disposed on the surface of the recess 230 of the substrate 23 which is sintered beforehand at 1600° C. for example, the cell, which also is sintered beforehand at 1500° C., for example, is disposed on the adhesive, and then the laminated cell 1 and the heater 3 are baked to a temperature lower than a sintering temperature of the substrate 23, for example 1100°–1200° C., thereby forming an intermediate layer 21 between the cell 1 and the heater 3. The intermediate layer 21 is not completely sintered, has a number of fine cracks of the order of $\mu$m, and presents an unglazed-like porcelain state. The thickness of the intermediate layer 21 is about 0.05 mm between the side wall portions 232 and about 0.2 mm at the side wall portions 232.

The thickness of the substrate 23 is about the same as the thickness of the cell 1. The thickness of the side wall portions 232 is about 1.5 times as thick as the cell 1 or thicker than the cell 1. The depth of the recess 230 is about ½ times the thickness of the cell 1 so that the diffusion chamber 9 for wide range fuel-air ratio signal generation cell part is completely embedded by the side wall portions 232 and the bottom surface 231 of the substrate 23 of the heater 3, except for the end surface provided with the diffusion chamber opening 13.

Thus formed, the oxygen sensor has an adhesion strength of about three times or higher adhesive strength at the abutment between the cell 1 and the heater 3 as compared with an oxygen sensor in which a cell is joined to a heater without such side wall portions as mentioned above. When the oxygen sensor is heated, both the cell 1 and the heater 3 expand, and since the solid-electrolyte body 5 of $Y_2O_3$-stabilized $ZrO_2$ is larger in thermal expansion coefficient than the substrate 23 of $Al_2O_3$ the cell 1 presses the intermediate layer 21 with cracks on the side wall portions 232, so that the cell 1 and the heater 3 are brought into a tight or close contact, with the cracks of the intermediate layer 21 being tightly closed. The intermediate layer 21 on the bottom surface 231 of the recess 230 also is pressed by the cell 1 and the heater 3 due to expansion of them, therefore, the cell 1 is brought into a tight or close contact with the heater 3 at the bottom surface 231 of the recess 230, as a whole the cell 1 is brought into a tight contact with the heater 3. When the sensor is cooled from such a state, the intermediate layer 21 restores the original states of the cracks. This behavior of this intermediate layer 21 enables it to absorb stresses caused by thermal shock received by the oxygen sensor. The intermediate layer 21 has an intermediate thermal expansion coefficient between these of the cell 1 and the heater 3, for example, the ratio of the thermal expansion coefficient of the $Al_2O_3$:$ZrO_2$:the intermediate layer $21 = 7:22:10-15$. Therefore, the intermediate layer 21 reduces thermal stresses caused in the cell 1 and the heater 3 due to difference in thermal expansion between the cell 1 and the heater 3.

As mentioned above, the cell 1 is formed mainly of $Y_2O_3$-stabilized $ZrO_2$, while the heater is formed mainly of $Al_2O_3$, and these are sintered beforehand respectively. A compound containing $Al_2O_3$ as a main agent, and $ZrO_2$, SiO, MgO or the like is used as an aid to bonding or sintering them. Specifically, an aqueous 1 liquid type paste-like bonding agent formed of 95% $Al_2O_3$, 4% $ZrO_2$ and 1% SiO is used. A compound other than the above which includes 50-95% $Al_2O_3$, 50-4% $ZrO_2$ and at least one of SiO and MgO as the remaining also can be used for joining the heater 3 to the cell 1.

The heater 3 and the cell 1 are sintered in appropriate sintering processes respectively, and then they may be bonded thereafter by a bonding agent containing $Al_2O_3$ as its main agent, $ZrO_2$, SiO or MgO as a bonding aid.

The cell 1 is composed of the theoretical air-fuel ratio point detection cell part and the wide-range air-fuel ratio function signal generating cell part, and the latter is so disposed that it may closely contact the u-shaped section of the heater 3, while the former is so disposed that it may be superposed in a layer on the latter. Thus, the heater 3 is joined directly to the cell part outputting a fuel-air ratio proportional signal; thereby the heat controllability is improved and both cell parts can be improved in temperature dependence.

Figure 13A:
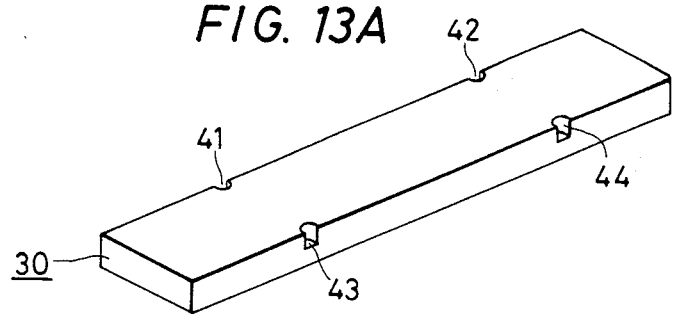
FIG. 13A is a perspective view of a cell according to another embodiment of the present invention.
Figure 13B:
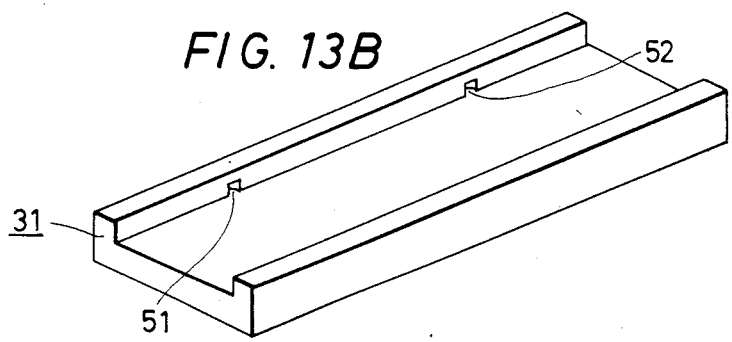
FIG. 13B is a perspective view of a heater according to another embodiment of the present invention.

FIGS. 13A and 13B show a cell 30 and a heater 31 which are provided with cavities 41 to 44, and 51 to 54, respectively. The cavities are filled with the substance of the intermediate layer or the bonding agent, so that a wedging effect is produced.

Figure 14:
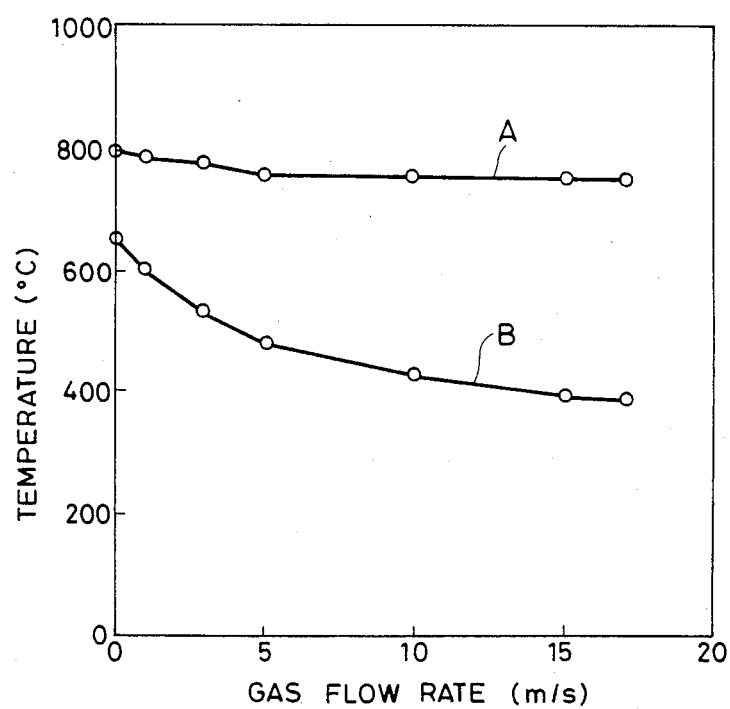
FIG. 14 is a graph showing relationships between temperature and gas flow rate.

As is seen from FIG. 14, the temperature on the surface of the cell 1 lowers with an increase in the speed of a gas flow, which is indicated by a characteristic curve B, while the temperature between the cell 1 and the heater 3 is maintained virtually at a fixed level, which is indicated by a characteristic curve A.

Though the above embodiments are described about the cell 1 in which two cell parts are superposed in layers, it is a matter of course that a cell of only one cell part (for example either one part of the above-mentioned two cell parts) can be used for the present invention.

It is also possible that the cell is provided with recesses, an inclination, a stage portion or others in the direction of the thickness thereof so that the form of the bonding agent may have wedging effect for the cell after it is set, and that the heater is also provided with such recesses, an inclination, a staged portion or others as aforesaid on both sides of the u-shaped section thereof.

What is claimed is:

1. An oxygen sensor, which includes a cell comprising a solid-electrolyte body having oxygen ion conductivity, a detection electrode disposed on one surface of said solid-electrolyte body so that said detection electrode is exposed to a gas to be detected, a reference electrode provided on said solid-electrolyte body so as to be opposed to said detection electrode through at least a part of said solid-electrolyte body, and a chamber provided to enclose said reference electrode, said chamber having an opening through which said chamber communicates with the gas to be detected; and a heater for heating said cell to a prescribed temperature, characterized in that said heater has a recess for receiving therein said cell, thereby providing a pair of side wall portions at both the sides of said heater, and said cell is disposed in said recess of said heater so that a part of each side of said cell is covered by said side wall portion of said heater and said opening of said chamber is disposed around one end of said heater to be exposed to the gas to be detected, and joined to said heater with an intermediate layer which is provided on the surface of said recess and has a thermal expansion coefficient of an intermediate value between these of said solid-electrolyte body and said heater.

2. The oxygen sensor as defined in claim 1, wherein said solid-electrolyte body is formed mainly of $Y_2O_3$-stabilized $ZrO_2$, said heater comprises an electrically insulating substrate formed mainly of $Al_2O_3$ and a heating element embedded in said substrate, and said intermediate layer is made by sintering a mixture, in paste form, comprising $Al_2O_3$ and $ZrO_2$ at a temperature less than a sintering temperature of $Al_2O_3$.

3. The oxygen sensor as defined in claim 2, wherein said intermediate layer has a number of fine cracks, thereby absorbing stresses caused by thermal shock in said solid-electrolyte body and said substrate.

4. An oxygen sensor comprising a solid-electrolyte body having oxygen ion conductivity, said solid-electrolyte body being elongated and substantially rectangular in a cross-section perpendicular to the length direction; first and second chambers formed in said solid-electrolyte body so as to extend substantially in parallel with each other along the length direction, and having openings; a detection electrode disposed on one surface of said solid-electrolyte so as to be exposed to gas to be detected; first and second reference electrodes mounted on said solid-electrolyte body to be exposed in said first and second chambers, respectively, thereby forming a first cell part by said detection electrode, said first reference electrode and a part of said solid-electrolyte body disposed therebetween, and a second cell part by said detection electrode, said second reference electrode and another part of said solid-electrolyte body; and a heater for heating said first and second cell parts, said heater formed of an electrically insulating substrate and a heating element embedded in said substrate, characterized in that said heater has a recess extending along the length direction of said solid-electrolyte body, thereby providing at both sides of said recess, a pair of side wall portions extending along the length direction of said recess, said solid-electrolyte body is disposed in said recess of said heater so that said openings of said chambers are positioned around the end of said heater, and an intermediate layer, provided between said solid-electrolyte body and said heater, and joining said heater to said solid-electrolyte body through sintering of said intermediate layer, said sintered intermediate layer having a number of fine cracks made therein and an intermediate thermal expansion coefficient between these of said solid-electrolyte body and said substrate of said heater.

5. The oxygen sensor as defined in claim 4, wherein said first and second cell parts are a theoretical air-fuel ratio point detection cell and a wide-range air-fuel ratio signal generating cell, respectively, and said second cell is disposed in said recess of said heater whereby said first cell is heated by said heater through said second cell.

6. The oxygen sensor as defined in claim 5, wherein said intermediate layer comprises $Al_2O_3$ as a main component thereof $ZrO_2$ and one element selected from a group consisting of $SiO_2$ and $MgO$, while said solid-electrolyte body is formed mainly of $Y_2O_3$-stabilized $ZrO_2$ and said substrate is formed mainly of $Al_2O_3$.

7. The oxygen sensor as defined in claim 6, wherein said solid-electrolyte and said various electrodes form said cell which is plate-shaped, said heater is formed in a plate whose one surface is recessed, and about one half of the thickness of said cell unit is covered by said side wall portions of said heater.

8. The oxygen sensor as defined in claim 7, wherein each of said wall portions has a thickness thicker than the thickness of said cell.

9. The oxygen sensor as defined in claim 6 wherein said intermediate layer comprises 50-95 wt % $Al_2O_3$ and 50-4 wt % $ZrO_2$.

10. The oxygen sensor as defined in claim 9, wherein said intermediate layer is sintered at a temperature lower than a sintering temperature of said substrate.

11. The oxygen sensor as defined in claim 4, wherein said cell and said heater have a plurality of cavities filled with part of said intermediate layer.

* * * * *